United States Patent [19]

Parker

[11] 4,122,191
[45] Oct. 24, 1978

[54] ANTIRHINOVIRUS AGENTS
[75] Inventor: Roger Alan Parker, Cincinnati, Ohio
[73] Assignee: Richardson-Merrell Inc., Wilton, Conn.
[21] Appl. No.: 751,140
[22] Filed: Dec. 20, 1976
[51] Int. Cl.² ............................................ A61K 31/12
[52] U.S. Cl. ................................................. 424/331
[58] Field of Search ............................... 424/331, 340
[56] References Cited
PUBLICATIONS
Chemical Abstracts 78: 71651j (1973).

*Primary Examiner*—Jerome D. Goldberg
*Attorney, Agent, or Firm*—L. Ruth Hattan; E. O. Retter; George W. Rauchfuss, Jr.

[57] ABSTRACT

Compounds of the following general structure are useful as antirhinovirus agents:

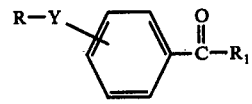

wherein Y is a bond, oxygen or divalent sulfur; R is a straight or branched hydrocarbon chain having from 6 to 20 carbon atoms and is saturated or unsaturated having from 1 to 4 double bonds when R has from 10 to 20 carbon atoms and 1 or 2 double bonds when R has from 6 to 9 carbon atoms; and $R_1$ is hydrogen or a straight or branched alkyl group of from 1 to 4 carbon atoms.

15 Claims, No Drawings

ANTIRHINOVIRUS AGENTS

FIELD OF INVENTION

This invention relates to substituted benzaldehydes and substituted phenyl alkyl ketones useful as antirhinovirus agents.

SUMMARY OF INVENTION

Compounds of the following general Formula I are useful as antirhinovirus agents:

Formula I

In the above general Formula I Y is a bond, oxygen or divalent sulfur; R is a straight or branched saturated hydrocarbon group having from 6 to 20 carbon atoms or a straight or branched unsaturated hydrocarbon group having from 6 to 20 carbon atoms and from 1 to 4 double bonds when R has from 10 to 20 carbon atoms and 1 or 2 double bonds when R has from 6 to 9 carbon atoms; and $R_1$ is hydrogen or a straight or branched lower alkyl group of from 1 to 4 carbon atoms.

DETAILED DESCRIPTION OF INVENTION

It is evident from the above general Formula I that the compounds employed in the present invention are substituted benzaldehydes and substituted phenyl alkyl ketones, and the substituent group R—Y— may be attached at the ortho, meta or para positions of the benzene ring.

In the above general Formula I the substituent R is a straight or branched saturated hydrocarbon group having from 6 to 20 carbon atoms in which case the R—Y— group may be represented as $C_qH_{2q+1}Y-$ wherein Y is a bond, oxygen or divalent sulfur, and $q$ is an integer of from 6 to 20, and the hydrocarbon group is straight or branched; or R is a straight or branched unsaturated hydrocarbon group having from 6 to 20 carbon atoms and from 1 to 4 double bonds when R has from 10 to 20 carbon atoms and 1 or 2 double bonds when R has from 6 to 9 carbon atoms in which case the R—Y— group may be represented as $C_qH_{2q-z}Y-$ wherein Y is a bond, oxygen or divalent sulfur, $q$ is an integer of from 6 to 20 and z is the integer 1, 3, 5 or 7 as the number of double bonds varies from 1 to 4 respectively when R has from 10 to 20 carbon atoms and z is 1 or 3 as the number of double bonds varies from 1 to 2 respectively when R has from 6 to 9 carbon atoms, and the hydrocarbon chain is straight or branched.

Illustrative examples of straight or branched saturated hydrocarbon groups which R may represent are, for example, decyl, undecyl, dodecyl, tridecyl, tetradecyl, 3,7-dimethyloctyl, 2,4-diethylnonyl, 1-methylundecyl, pentadecyl, hexadecyl, heptadecyl 3-methyloctadecyl, nonadecyl, didecyl, nonyl, octyl, heptyl and hexyl.

Illustrative examples of straight or branched unsaturated hydrocarbon groups containing from 1 to 4 double bonds which R may represent are, for example, 10-undecenyl, 9,12-octadecyldienyl, 3,7,11-trimethyl-2,6,10-hexadecyltrienyl, 3,7-dimethyl-2,6-octadienyl, 5,9-dimethyl-2,4,8-decatrienyl, 4,6-dimethyloct-3-enyl, 1,2,5,9-tetramethyl-2,4,8-decatrienyl, 11-didecenyl and 2-hexenyl.

Illustrative examples of straight or branched lower alkyl groups of from 1 to 4 carbon atoms which $R_1$ may represent are methyl, ethyl, n-propyl, isopropyl, n-butyl and tert-butyl.

A preferred embodiment of this invention is the use of compounds of general Formula I as antirhinovirus agents wherein $R_1$ is a straight chain alkyl group with $R_1$ as methyl being more preferred. Another preferred embodiment is the use of compounds of general Formula I as anti-rhinovirus agents wherein R has from 6 to 12 carbon atoms with an 8 to 10 carbon atom chain length being more preferred. The use of compounds of general Formula I wherein Y is oxygen or a bond is another preferred embodiment with Y as a bond being more preferred. Also, the use of compounds of general Formula I as antirhinovirus agents wherein the R—Y— group is attached to the phenyl ring at the meta or para positions are preferred with substitution at the para position being more preferred.

Illustrative examples of compounds of general Formula I are the following:

p-n-hexylbenzaldehyde,
m-n-octyloxybenzaldehyde,
o-n-decylthiobenzaldehyde,
p-n-undecylbenzaldehyde,
p-n-dodecyloxybenzaldehyde,
m-n-tridecylthiobenzaldehyde,
o-11-didecenylbenzaldehyde,
p-n-hexenyloxybenzaldehyde,
p-1,2,5,9-tetramethyl-2,4,8-decatrienyloxybenzaldehyde,
m-4,6-dimethyloct-3-enylthiobenzaldehyde,
p-5,9-dimethyl-2,4,8-decatrienyloxybenzaldehyde,
p-n-hexadecyloxybenzaldehyde,
m-n-pentadecyloxybenzaldehyde,
p-n-octadecylthiobenzaldehyde,
p-n-didecyloxyphenyl methyl ketone,
m-n-nonadecylthiophenyl ethyl ketone,
o-n-heptadecyloxyphenyl n-propyl ketone,
o-n-hexadecylphenyl methyl ketone,
p-n-tridecylphenyl ethyl ketone,
p-n-tetradecyloxyphenyl methyl ketone,
p-n-tetradecylthiophenyl methyl ketone,
m-n-tetradecyloxyphenyl methyl ketone,
p-n-tetradecyloxyphenyl n-butyl ketone,
p-n-dodecyloxyphenyl methyl ketone,
p-n-dodecylthiophenyl isopropyl ketone,
m-n-dodecylphenyl tert-butyl ketone,
o-n-decyloxyphenyl ethyl ketone,
p-n-nonylthiophenyl methyl ketone,
p-n-hexyloxyphenyl n-propyl ketone,
m-n-heptylphenyl methyl ketone,
p-3,7-dimethyloctyloxyphenyl ethyl ketone,
m-2,4-diethylnonylthiophenyl methyl ketone,
o-3-methyloctadecylthiophenyl isopropyl ketone,
p-10-undecenyloxyphenyl n-butyl ketone,
m-9,12-octadecyldienylthiophenyl methyl ketone,
p-3,7,11-trimethyl-2,6,10-hexadecyltrienyloxyphenyl tert-butyl ketone, and
p-1-methylundecyloxybenzaldehyde.

The compounds of general Formula I are useful as antirhinovirus agents. The rhinovirus genus which is a member of the picornavirus family, contains over 100 different antigenic types, and is known to be responsible for many of the symptoms attendant respiratory infections. The name rhinovirus is indicative of the prominent nasal involvement seen in infections with these viruses resulting in syndromes characteristic of the common cold. Rhinoviruses have been classified as serotypes 1 to 89 and subtypes 1A (88, 89, 90) with at least 20 more types to be added to the classification. Experimental studies indicate nasal mucosa is more susceptible to rhinovirus than is the lower respiratory tract. The symptoms of rhinovirus infection have also been produced experimentally by dropping small amounts of the virus on the conjunctiva, indicating that the eye is another susceptible infectious site. Developed rhinovirus infection is characterized by hyperemia and edema of the mucous membrane with exudation of serous and mucinous fluid. The nasal cavities are narrowed by thickening of the membrane and engorgement of the turbinates.

The compounds described herein have been found to be effective antiviral agents against numerous types of rhinovirus rendering said compounds useful in treating the symptoms of a rhinovirus infection in hosts susceptible to said infections including humans and certain anthropoid apes such as the chimpanzee. It is known in the art that several test systems can be employed to measure antiviral activity against rhinovirus. For example, antirhinovirus activity can be measured using a plaque assay or tube test wherein the activity of the compound against virus challenge in a cell system is measured. Using a variety of test systems it is found that compounds of general Formula I are effective antirhinovirus agents when the test compound is given prior to, concurrently with or subsequent to virus challenge. The utility of the compounds described herein as antirhinovirus agents has been demonstrated in a variety of test systems. For example, using HeLa cell cultures to which a rhinovirus challenge of from 30 to 100 $TCID_{50}$ is added concurrently with test compounds at a concentration of 4, 20 or 100 $\mu$g/ml after which the cell cultures are incubated for 48 hours it was found upon microscopic examination of the cell cultures that compounds of general Formula I markedly inhibit the cytopathic effect of the virus when compared to cell cultures containing only virus challenge. For example, when the compound of Example 9 at a concentration of 4 $\mu$g/ml was added to cell cultures together with a rhinovirus challenge of 100 $TCID_{50}$ the cytopathic effect of virus was inhibited by 62% when compared to control.

In the treatment of symptoms of rhinovirus infection the compounds of general Formula I can be administered orally, topically, for example, intranasally, and parenterally, for example, intramuscularly. Topical administration is preferred. The compounds are administered preferably in the form of a pharmaceutical preparation to a host susceptible to rhinovirus infection either prior to or after invasion of virus or after onset of the infection. For prophylactic treatment it is contemplated that an antirhinovirus effective amount of compound be administered for from about 1 to 5 days prior to anticipated exposure to virus and from about 5 to 10 days subsequent to exposure or from about 5 to about 15 days subsequent to exposure to rhinovirus. It is known that rhinovirus is readily transmitted from one susceptible host to another as commonly occurs, for example, among family members, in classrooms and in military populations. The compounds of general Formula I are also useful therapeutically in treating antirhinovirus infections in that said compounds are effective in diminishing or blocking replication of the virus.

For prophylactic or therapeutic treatment of rhinovirus infection any antirhinovirus effective amount of a compound of general Formula I may be employed. For therapeutic treatment the amount of compound administered will vary depending primarily on the severity of the infection. For therapeutic or prophylactic treatment the amount of compound administered will vary from about 0.1 mg/kg to 15 mg/kg of body weight of the patient, that is, susceptible host. Preferably the amount of compound administered will vary from about 1 mg/kg to about 3 mg/kg. Typically a unit dose containing about 25 mg of compound administered from 1 to 6 times daily will achieve the desired effect.

The compounds of general Formula I together with suitable pharmaceutical carriers can be in the form of solid unit dosage forms such as tablets, capsules, powders, or in the form of a suppository. The powders can be administered orally or by insufflation. In the preparation of solid unit dosage forms it may be desirable to micronize the compound to be employed. In solid unit dosage forms the compounds can be combined with conventional carriers, for example, binders, such as acacia, corn starch or gelatin, disintegrating agents, such as, corn starch, potato starch or alginic acid, lubricants, such as, stearic acid or magnesium stearate, and inert fillers, such as, lactose, sucrose or corn starch.

The compounds of general Formula I may also be administered as liquid suspensions or solutions using a sterile liquid, such as, an oil, or water with or without the addition of a pharmaceutically suitable surfactant or emulsifying agent for oral, topical or parenteral administration. A particularly suitable mode of administration is a liquid formulation of the compounds applied directly to the nasal cavity, for example, in the form of a nose drop. For liquid preparations the compounds can be suitably formulated with fixed oils, such as, peanut oil, sesame oil, cottonseed oil or olive oil. Peanut oil and sesame oil are particularly useful in preparation of formulations for intramuscular injection. Such oils can also be employed in the preparation of formulations of the soft gelatin type and suppositories. In general, water, saline, aqueous dextrose and related sugar solutions and glycerols, such as, polyethyleneglycol may be employed in the preparation of liquid formulations which may suitably contain suspending agents, such as, methyl cellulose, hydroxypropyl cellulose or carboxymethyl cellulose as well as buffers and preservatives.

Illustrative examples of suitable pharmaceutical formulations are set forth hereinbelow.

The compounds of general Formula I wherein $R_1$ is hydrogen and R is a straight or branched saturated hydrocarbon chain having from 60 to 20 carbon atoms may be prepared by chemical or catalytic reduction of the corresponding R—Y— substituted benzoic acid halide or tertiary benzamide by methods generally described in J. March, *Advanced Organic Chemistry: Reactions, Mechanisms and Structure*, McGraw-Hill, pp. 351, 352 and 684 (1968). Reduction of the corresponding benzoyl halides, for example, the benzoyl chloride, using a catalytic hydrogenation method to give the aldehyde compound is known as the Rosenmund reduction and is the most common way to prepare the aldehydes. A suitable catalyst for this reaction is palladium-$BaSO_4$ in a ratio of 1 part catalyst to 5 to 10 parts of acid chloride. This reaction may be carried out with or without a regulator, such as, quinoline sulfur. Suitable solvents for this reaction are dry solvents selected from aromatic hydrocarbons, such as, benzene, toluene and xylene, non-aromatic hydrocarbons, such as, decalin and ethers, such as, diethylether. This reaction may be carried out at temperatures of from room temperature, that is, about 25° C. to the reflux temperature of the solvent, and the reaction time varies from about 15 minutes to 24 hours.

The compounds of general Formula I wherein $R_1$ is hydrogen and R is a straight or branched unsaturated hydrocarbon chain having from 6 to 20 carbon atoms may be prepared by reduction of the corresponding R—Y— substituted tertiary benzamide or benzoyl halide using a metal hydride reducing agent. This reaction can be carried out in ether solvents, such as, diethylether, tetrahydrofuran, dioxane and glyme, or, hydrocarbon solvents, such as, benzene and toluene. The reaction temperature may vary from 0° C. to the reflux temperature of the solvent and the reaction time may vary from about 15 minutes to 24 hours.

The compounds of general Formula I wherein $R_1$ is hydrogen may also be prepared by reducing the corresponding nitrile by two principal methods, one such method being known as the Stephen reduction, using hydrochloric acid and tin chloride and the other method employing a metal hydride reducing agent. In the Stephen reduction, ether solvents, such as, diethylether and dioxane can be employed and the ether solvent can be saturated with hydrochloric acid to provide a source of HCl required for the reaction. The reaction can be carried out at temperatures of from about 25° C. to the reflux temperature of the solvent, and the reaction time can vary from about 15 minutes to 24 hours. Reduction of the nitrile using a metal hydride reducing agent, such as, $LiAlH_4$ or $NaAlH_2(OCH_2CH_2OCH_3)_2$ can be carried out in ether solvents, such as, diethylether, tetrahydrofuran, dioxane and glyme, or hydrocarbon solvents, such as, toluene and benzene. The reaction temperature can vary from 0° C. to the reflux temperature of the solvent, and the reaction time can vary from about 15 minutes to 24 hours. The reduction reaction is followed by acid hydrolysis by, for example, adding aqueous hydrochloric acid to the reaction mixture.

The ketone compound of general Formula I, that is, compounds wherein $R_1$ is a straight or branched alkyl group of from 1 to 4 carbon atoms may be prepared by treating one equivalent of the corresponding R—Y— substituted benzoic acid derivative with two equivalents of an appropriate alkyllithium as generally described by Fieser and Fieser, *Reagents for Organic Synthesis*, J. Wiley and Sons, Inc., New York, p. 688 (1967). This reaction is suitably carried out in solvents, such as, ether, tetrahydrofuran, p-dioxane, dimethoxyethane or diethyleneglycol dimethylether at temperatures of from −10° C. to the reflux temperature of the solvent for from ½ hour to 10 hours.

The ketone compounds of general Formula I may also be prepared by the reaction of alkyl magnesium bromide wherein the alkyl moiety is straight or branched and has from 1 to 4 carbon atoms, and the imidazolide derivative of an appropriately R—Y— substituted benzoic acid derivative wherein R and Y have the meanings defined in general Formula I. This reaction is carried out in solvents such as ether, tetrahydrofuran, dioxane, dimethoxyethane, or acetonitrile. The reaction mixture is initially cooled to −10° C. after which the temperature is elevated to from about 25° C.

to the reflux temperature of the solvent; and the reaction time varies from about ½ hour to 10 hours. The imidazolide derivative is obtained by treating an appropriately R—Y— substituted benzoic acid derivative with N,N′-carbonyldiimidazole or by treatment of the R—Y— substituted benzoyl chloride, obtained by treating the substituted benzoic acid with thionyl chloride, with two equivalents of imidazole as generally described by H. A. Staab, Angew. Chem. Internat. Edit. 1 351 (1962).

The ketone compounds of general Formula I wherein the R—Y— substituent group is attached at the para-position of the phenyl ring may also be prepared by a Friedel-Crafts acylation of an appropriately R—Y— substituted phenyl, wherein R and Y have the meanings defined in general Formula I, with an acyl halide of the formula

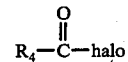

wherein halo is halogen, preferably chlorine or bromine, and $R_4$ is a straight or branched alkyl group of from 1 to 4 carbon atoms. This reaction is carried out in the presence of an acid catalyst, for example, borontrifluoride-etherate, stannic chloride, zinc chloride, hydriodic acid or orthophosphoric acid and optionally in the presence of a solvent, for example, methylene chloride, nitromethane or benzene. Suitable temperatures for this reaction vary from −20° C. to the reflux temperature of the solvent, and the reaction time varies from about ½ hour to 10 hours.

The R—Y— substituted benzoyl halides, benzamides, and benzonitriles used hereinabove can be prepared by procedures generally known in the art. The benzamide derivatives can be isolated or formed in situ. The corresponding R—Y— substituted benzoic acid derivatives are known in the art or can be prepared by several methods. For example, the R—Y— substituted benzoic acids wherein Y is oxygen or divalent sulfur can be prepared by the Williamson reaction, as generally described in the above cited March reference at page 316, as illustrated by the following reaction sequence:

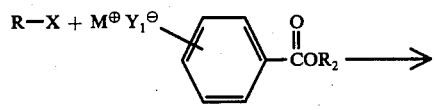

structure 1

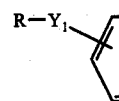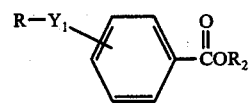

structure 2

In the above reaction sequence, X represents a halogen atom, such as, chlorine, bromine or iodine; $M^\oplus$ represents a metal salt, such as, lithium, sodium, potassium, silver or mercury; $R_2$ is lower alkyl, such as, methyl and ethyl; R has the meaning defined in general Formula I; and $Y_1$ is oxygen or divalent sulfur. In the compounds of structures 1 and 2 the substituent groups $M^\oplus Y_1^-$— and R—$Y_1$— can be attached at the ortho-, meta- or para-positions of the benzene ring. The above reaction may be carried out with or without solvents. Suitable solvents for this reaction include lower alcohols such as ethanol and isopropyl alcohol, or ketones, such as, acetone and methyl isobutyl ketone, or amides, such as, dimethylformamide and dimethylacetamide. Other suitable solvents include dimethylsulfoxide, acetonitrile, and dimethoxyethane. The temperature of the reaction may vary from about 25° C. to the reflux temperature of the solvent, and the reaction time may vary from about 1 hour to 80 hours. The phenoxide metal salts, as represented by the compounds of structure 1, are preferably formed in situ by the addition of a base such as, sodium methoxide, potassium carbonate, or potassium hydroxide to the corresponding hydroxy phenyl or mercapto phenyl derivative. The esters of structure 2 are hydrolyzed to the corresponding carboxylic acids by procedures generally known in the art.

In the above reaction in place of the compounds as represented as R—X, R-methane sulfonates and R-p-toluene sulfonates wherein R has the meaning defined in general Formula I may be used.

The corresponding benzoic acid derivatives wherein Y is oxygen or divalent sulfur may also be prepared by displacement of a leaving group of a benzoate compound with a metal alkoxide or metal thioalkoxide as illustrated by the following:

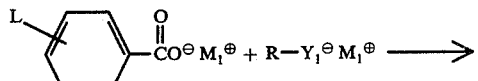

structure 3    structure 4

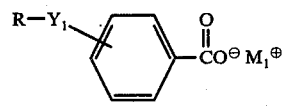

structure 5

In the above reaction, L represents a leaving group, such as, a diazo salt or a halide such as bromide or iodide; $M_1^{\oplus}$ represents a metal salt, such as, potassium, sodium, or lithium; R has the meaning defined in geneal Formula I; and $Y_1$ is oxygen or divalent sulfur. The above illustrated displacement may be carried out in the absence of a solvent resulting in a fusion reaction, or in the presence of a high boiling inert solvent such as dimethylformamide, dimethylsulfoxide or dimethylacetamide. The salts of structure 5 are acidified to give the corresponding carboxylic acids.

The above described Williamson ether reaction can also be employed to prepare the aldehyde derivatives described herein wherein Y is oxygen or divalent sulfur as illustrated by the following reaction sequence:

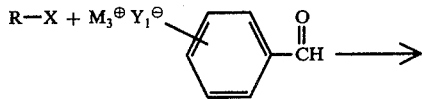

structure 6

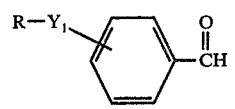

structure 7

In the above reaction sequence, R has the meanings defined in general Formula I; $Y_1$ is oxygen or divalent sulfur; X is as defined hereinabove; and $M_3^{\oplus}$ represents a metal salt, such as, lithium, calcium, potassium, sodium silver, and mercury. The $M_3^{\oplus}$—$Y_1^{-}$— and the R—$Y_1$— substituents in structures 6 and 7 respectively may be attached at the ortho-, meta- or para- positions of the phenyl ring. The reaction conditions for this ether synthesis are the same as described hereinabove for the preparation of the compounds of structure 1.

The benzoic acid derivatives employed herein wherein Y is a bond are known in the art or may be obtained by several methods known in the art. For example, the compounds can be obtained by nitration of an appropriately R—Y— substituted phenyl derivative wherein Y is a bond and subsequently reducing the thus obtained nitro derivative using, for example, hydrazine to the aniline derivatives which are treated under conditions of a Sandmeyer reaction using cuprous cyanide followed by acid or base hydrolysis to give the R—Y— substituted benzoic acids wherein Y is a bond and R has the meaning defined in general Formula I.

The R—Y— substituted benzoic acids wherein Y is a bond and the R—Y— group is attached at the ortho or meta position of the phenyl ring may also be prepared by nitration of a derivative of the formula

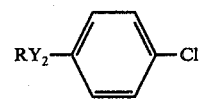

wherein $Y_2$ is a bond and R has the meaning defined in general Formula I and reducing the thus obtained nitro derivatives to the declorinated aniline derivative by metal hydride reduction or by using hydrazine and palladium. The aniline derivatives are then treated as described above, that is, treated under conditions of a Sandmeyer reaction using cuprous cyanide followed by acid or base hydrolysis.

The R—Y— substituted phenyl derivatives employed herein are known in the art or may be obtained by various methods known in the art. For example, the R—Y— substituted phenyl derivatives wherein Y is a bond may be obtained by reacting an appropriate alcohol and benzene under conditions of a Friedel-Crafts alkylation reaction. The R—Y— substituted phenyl derivatives wherein Y is oxygen or divalent sulfur may be obtained by the Williamson reaction described hereinabove for preparing compounds of structure 2 by reaction of a phenylalcohol or phenylthioalcohol with an appropriate alkylating reagent, R—X wherein R has the meaning defined in general Formula I and X is chlorine, bromine or iodine.

The following specific examples are illustrative of the compounds described herein.

EXAMPLE 1

4-(Decyloxy)benzaldehyde

To a mixture of 27.8 g (0.1 mole) of 4-(decyloxy)benzoic acid in 500 ml of tetrahydrofuran cooled to 0° C. is slowly added 16.2 g (0.1 mole) of N,N'-carbonyldiimidazole. The mixture is heated to reflux for 1 hour then cooled to −20° C. To the cooled mixture is added 1.9 g (0.05 mole) of lithium aluminum hydride and stirring is continued at −20° C. for 1 hour. To the reaction mixture is slowly added 100 ml of 5% aqueous hydrochloric acid followed by the addition of ether. The ether layer is separated and washed with 5% aqueous bromotetradecane and p-hydroxybenzaldehyde the respective products listed in Table II are obtained.

TABLE II

| ALKYL HALIDE | ALDEHYDE | PRODUCT |
| --- | --- | --- |
| 1-chlorodecane | a-mercaptobenzaldehyde | 2-decylthiobenzaldehyde |
| 1-bromohexane | m-hydroxybenzaldehyde | 3-hexyloxybenzaldehyde |
| 1-bromododecane | m-hydroxybenzaldehyde | 3-dodecyloxybenzaldehyde |
| 1-bromotetradecane | o-mercaptobenzaldehyde | 2-tetradecylthiobenzaldehyde |
| 1-bromooctane | o-hydroxybenzaldehyde | 2-octyloxybenzaldehyde |
| 1-chlorohexadecane | p-mercaptobenzaldehyde | 4-hexadecylthiobenzaldehyde |
| 1-bromononadecane | p-hydroxybenzaldehyde | 4-nonadecyloxybenzaldehyde |
| 1-bromohexane | p-mercaptobenzaldehyde | 4-hexlthiobenzaldehyde |
| 1-bromo-3,7-dimethyl-6-octene | p-hydroxybenzaldehyde | 4-(3,7-dimethyl-6-octenyl-oxy)benzaldehyde |
| 1-chloro-2-decene | o-hydroxybenzaldehyde | 2-(2-decenyloxy)benzaldehyde |
| 1-bromo-10-undecene | p-hydroxybenzaldehyde | 4-(10-undecenyloxy)benzaldehyde |
| 1-bromo-1,2,5,9-tetramethyl-2,4,8-decatriene | p-mercaptobenzaldehyde | 4-(trans,trans-1,2,5,9-tetramethyl-2,4,8-decatrienyl-thio)benzaldehyde |
| 1-bromo-3-methyloctadecane | o-mercaptobenzaldehyde | 2-(3-methyloctadecylthio)-benzaldehyde | hydrochloric acid, water, and 5% aqueous sodium bicarbonate then dried over sodium sulfate, filtered and evaporated to dryness to give 4-(decyloxy)benzaldehyde.

EXAMPLE 2

4-Tetradecyloxybenzaldehyde

To a stirred mixture of 50 g (0.41 mole) of p-hydroxybenzaldehyde, 22.2 g (0.41 mole) of sodium methoxide and 500 ml of dried dimethylformamide was added 114 g (0.41 mole) of 1-bromotetradecane. The mixture was refluxed for 3 hours, then allowed to stand at room temperature overnight after which it was poured into ice-water and extracted with diethyl ether. The ether layer was washed with water, 5% potassium hydroxide, and saline, and dried over sodium sulfate, filtered and evaporated. The residue is recrystallized from hexane to give 4-tetradecyloxybenzaldehyde.

EXAMPLE 3

When in the procedure of Example 1 an appropriate amount of 4-tetradecyloxybenzoic acid, 4-(cis,cis-9,12-octadecadienylthio)benzoic acid, 3-tetradecylthiobenzoic acid, 3-hexadecylthiobenzoic acid, 3-octadecylthiobenzoic acid, 3-didecylthiobenzoic acid, 3-tridecylthiobenzoic acid, 4-hexyloxybenzoic acid, 3-octylthiobenzoic acid, 4-hexylbenzoic acid, 4-decylbenzoic acid, or 3-tetradecylbenzoic acid is substituted for 4-decyloxybenzoic acid the following respective products are obtained:

4-tetradecyloxybenzaldehyde,
4-(cis,cis-9,12-octadecadienylthio)benzaldehyde,
3-tetradecylthiobenzaldehyde,
3-hexadecylthiobenzaldehyde,
3-octadecylthiobenzaldehyde,
3-didecylthiobenzaldehyde,
3-tridecylthiobenzaldehyde,
4-hexyloxybenzaldehyde,
3-octylthiobenzaldehyde,
4hexylbenzaldehyde,
4-decylbenzaldehyde, and
3-tetradecylbenzaldehyde.

When in the procedure of Example 2 appropriate amounts of an alkyl halide and an aldehyde listed in the following Table II are substituted respectively for 1-

EXAMPLE 4

| Solution | | |
| --- | --- | --- |
| Methyl 1-(4-decyloxy)phenyl ketone | 0.85 | g |
| Alcohol | 78.9 | ml |
| Isopropyl Myristate | 5.0 | g |
| Polyethylene Glycol 400 | 10.0 | g |
| Purified Water qs ad | 100 | ml |

Combine the alcohol, isopropyl myristate and polyethylene glycol 400 and dissolve the drug substance therein. Add sufficient purified water to give 100 ml.

EXAMPLE 5

| Tablet | For 15,000 | |
| --- | --- | --- |
| Methyl 1-(4-hexyloxy)phenyl ketone | 75 | g |
| Lactose | 1.216 | Kg |
| Corn Starch | 0.3 | Kg |

Mix the active ingredient, the lactose and corn starch uniformly. Granulate with 10% starch paste. Dry to a moisture content of about 2.5%. Screen through a No. 12 mesh screen. Add and mix the following:

| Magnesium Stearate | 0.015 Kg |
| --- | --- |
| Corn Starch qs ad | 1.725 Kg |

Compress on a suitable tablet machine to a weight of 0.115 g/tablet.

EXAMPLE 6

| Soft Gelatin Capsule | |
| --- | --- |
| 4-decylbenzaldehyde | 0.25 Kg |
| Polysorbate 80 | 0.25 Kg |
| Corn Oil qs ad | 25.0 Kg |

Mix and fill into 50,000 soft gelatin capsules.

EXAMPLE 7

| IM Injections | | |
| --- | --- | --- |
| A. Oil Type: | | |
| 3-octyloxybenzaldehyde | 25 | mg |
| BHA, BHT aa | 0.01% | w/v |
| Peanut Oil or Sesame Oil qs | 1.0 | ml |
| B. Suspension Type: | | |
| Methyl 1-(4-hexylthio)phenyl ketone micronized | 25 | mg |

-continued

| IM Injections | | |
|---|---|---|
| Sodium Carboxymethylcellulose | 0.5% | w/v |
| Sodium Bisulfite | 0.02% | w/v |
| Water for Injection, qs | 1.0 | ml |

EXAMPLE 8

| Powder | |
|---|---|
| | % w/w |
| Methyl 1-(4-decyloxy)phenyl ketone | 1 |
| Silicon dioxide, anhydrous | 0.5 |
| Corn starch, lactose, fine powder aa | qs |

EXAMPLE 9

Methyl 1-(4-hexyl)phenyl ketone

To a mixture of 203 g of n-hexylbenzene, 184 g of anhydrous aluminum chloride and 1 liter of carbon tetrachloride cooled in an ice bath is slowly added 108.5 g of acetyl chloride, and the reaction mixture is refluxed with stirring for 1 hour then cooled and poured into ice-concentrated hydrochloric acid. The organic layer is separated, washed with water and brine, dried over sodium sulfate and distilled under vacuum to give methyl 1-(4-hexyl)phenyl ketone, b.p. 150°–153° C. at 3.1 mm Hg.

EXAMPLE 10

Methyl 1-(4-decyloxy)phenyl ketone

To a mixture of 27.8 g (0.1 mole) of 4-decyloxybenzoic acid and 300 ml of anhydrous ether stirred at room temperature is slowly added with stirring 100 ml of 2 M methyllithium in ether. The reaction mixture is stirred at room temperature for 2 hours then poured into 1 liter of a saturated ammonium chloride solution. The organic layer is separated, washed with 5% sodium bicarbonate and brine and evaporated to dryness to give a low melting solid which is recrystallized from hexane to give methyl 1-(4-decyloxy)phenyl ketone, M.P. 38°–39° C.

When in the procedure of Example 10 an appropriate amount of an acid listed in the following Table I is substituted for 4-decyloxybenzoic acid the respective ketone derivatives listed in Table I are obtained.

TABLE I

| ACID | KETONE |
|---|---|
| 3-n-tetradecyloxybenzoic acid | methyl 1-(3-n-tetradecyloxy)phenyl ketone, M.P. 36–37° C |
| 4-n-tetradecyloxybenzoic acid | methyl 1-(4-n-tetradecyloxy)phenyl ketone, M.P. 58–59° C |
| 3-n-hexadecyloxybenzoic acid | methyl 1-(3-n-hexadecyloxy)phenyl ketone, M.P. 45–46° C |
| 4-n-tridecyloxybenzoic acid | methyl 1-(4-n-tridecyloxy)phenyl ketone, M.P. 59–60° C |
| 4-n-octylbenzoic acid | methyl 1-(4-n-octyl)phenyl ketone, b.p. 142° C (0.05 mm Hg) |
| 4-n-hexadecyloxybenzoic acid | methyl 1-(4-n-hexadecyloxy)phenyl ketone, M.P. 65–67° C |
| 4-n-octadecyloxybenzoic acid | methyl 1-(4-n-octadecyloxy)phenyl ketone, M.P. 72–73° C |
| 4-n-dodecyloxybenzoic acid | methyl 1-(4-n-dodecyloxy)phenyl ketone, M.P. 48–50° C |
| 4-n-pentadecyloxybenzoic acid | methyl 1-(4-n-pentadecyloxy)phenyl ketone, M.P. 66–67° C |
| 4-n-decylthiobenzoic acid | methyl 1-(4-n-decylthio)phenyl ketone |
| 3-n-octylthiobenzoic acid | methyl 1-(3-n-octylthio)- |

TABLE I-continued

| ACID | KETONE |
|---|---|
| | phenyl ketone |
| 4-n-hexylthiobenzoic acid | methyl 1-(4-n-hexylthio)phenyl ketone |

When in the procedure of Example 10 an appropriate amount of a straight or branched higher alkyllithium, for example, ethyllithium, isopropyllithium, or n-butyllithium is substituted for methyllithium the following respective products are obtained:

ethyl 1-(4-decyloxy)phenyl ketone,
isopropyl 1-(4-decyloxy)phenyl ketone, and
n-butyl 1-(4-decyloxy)phenyl ketone.

I claim:

1. A method for prophylaxis or treatment of a rhinovirus infection which comprises administering to a host susceptible to a rhinovirus infection an antirhinovirus effective amount of a compound of the formula

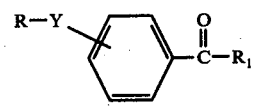

wherein Y is oxygen or divalent sulfur; $R_1$ is hydrogen or a straight or branched lower alkyl group having from 1 to 4 carbon atoms; and R is a straight or branched saturated hydrocarbon group having from 6 to 20 carbon atoms or a straight or branched unsaturated hydrocarbon group having from 6 to 20 carbon atoms and 1 to 4 double bonds when R has from 10 to 20 carbon atoms and 1 or 2 double bonds when R has from 6 to 9 carbon atoms.

2. The method of claim 1 wherein the R—Y— group is attached at the meta or para positions of the phenyl ring.

3. The method of claim 1 wherein the R—Y— group is attached at the para position of the phenyl ring.

4. The method of claim 1 wherein $R_1$ is a straight or branched lower alkyl group having from 1 to 4 carbon atoms.

5. The method of claim 4 wherein $R_1$ is a straight chain alkyl group.

6. The method of claim 5 wherein $R_1$ is methyl.

7. The method of claim 1 wherein R has from 6 to 12 carbon atoms.

8. The method of claim 7 wherein R has from 6 to 10 carbon atoms.

9. The method of claim 8 wherein R has 6 carbon carbon atoms.

10. The method of claim 1 wherein Y is oxygen.

11. The method of claim 1 wherein $R_1$ is a straight or branched lower alkyl group having from 1 to 4 carbon atoms; Y is oxygen; and R has from 6 to 12 carbon atoms.

12. The method of claim 11 wherein the R—Y group is attached at the meta or para positions of the phenyl ring.

13. The method of claim 11 wherein the compound is methyl 1-(4-decyloxy)phenyl ketone.

14. The method of claim 1 wherein the amount of compound administered is from about 0.1 mg/kg to about 15 mg/kg of body weight of host per day.

15. The method of claim 1 wherein the amount of compound administered is from about 1 mg/kg to about 3 mg/kg of body weight of host per day.

* * * * *